(12) United States Patent
Trinidad

(10) Patent No.: US 7,879,053 B2
(45) Date of Patent: Feb. 1, 2011

(54) BALLOON WITH STEPPED SECTIONS AND IMPLEMENTS

(75) Inventor: Jeffrey S. Trinidad, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 403 days.

(21) Appl. No.: 11/017,130

(22) Filed: Dec. 20, 2004

(65) Prior Publication Data

US 2006/0135980 A1    Jun. 22, 2006

(51) Int. Cl.
*A61B 17/22* (2006.01)
*A61M 29/02* (2006.01)

(52) U.S. Cl. ............. 606/159; 604/103.08; 604/103.09; 606/194

(58) Field of Classification Search ............... 604/96.01, 604/101.05, 103.06–103.09, 101.01, 103.07, 604/103.12, 101.5; 606/191–198, 159, 167, 606/180, 200; 623/1.11–1.54
See application file for complete search history.

(56) References Cited

U.S. PATENT DOCUMENTS

| | | | | |
|---|---|---|---|---|
| 4,445,509 A * | 5/1984 | Auth | ......................... | 606/159 |
| 5,226,887 A | 7/1993 | Farr et al. | ..................... | 604/96 |
| 5,320,634 A * | 6/1994 | Vigil et al. | ................. | 606/159 |
| 5,336,234 A | 8/1994 | Vigil et al. | ................. | 606/159 |
| 5,338,298 A | 8/1994 | McIntyre | ..................... | 604/96 |
| 5,372,601 A | 12/1994 | Lary | ......................... | 606/159 |
| 5,409,495 A | 4/1995 | Osborn | ...................... | 606/108 |
| 5,415,634 A | 5/1995 | Glynn et al. | ................. | 604/96 |
| 5,514,154 A * | 5/1996 | Lau et al. | ................... | 623/1.15 |
| 5,540,712 A * | 7/1996 | Kleshinski et al. | ......... | 623/1.19 |
| 5,616,149 A * | 4/1997 | Barath | ....................... | 606/159 |
| 5,649,941 A | 7/1997 | Lary | ......................... | 606/159 |
| 5,766,203 A * | 6/1998 | Imran et al. | ................. | 623/1.11 |
| 5,782,740 A * | 7/1998 | Schneiderman | ................ | 600/1 |
| 5,792,158 A | 8/1998 | Lary | ......................... | 606/159 |
| 5,797,935 A | 8/1998 | Barath | ........................ | 606/159 |
| 5,935,135 A * | 8/1999 | Bramfitt et al. | ............ | 623/1.11 |
| 6,030,405 A | 2/2000 | Zarbatany et al. | ........... | 606/191 |
| 6,120,523 A | 9/2000 | Crocker et al. | .............. | 606/192 |
| 6,197,013 B1 * | 3/2001 | Reed et al. | ................... | 604/509 |
| 6,258,099 B1 * | 7/2001 | Mareiro et al. | .............. | 606/108 |
| 6,258,108 B1 | 7/2001 | Lary | ......................... | 606/159 |
| 6,290,485 B1 | 9/2001 | Wang | ......................... | 425/470 |
| 6,352,551 B1 | 3/2002 | Wang | ........................ | 623/1.11 |

(Continued)

FOREIGN PATENT DOCUMENTS

EP    1 062 966 A1    12/2000

(Continued)

*Primary Examiner*—Anhtuan T Nguyen
*Assistant Examiner*—Kathleen Sonnett
(74) *Attorney, Agent, or Firm*—Seager, Tufte & Wickhem, LLC

(57) ABSTRACT

A catheter balloon may include a proximal waist portion, a proximal cone portion, a first body portion, a second body portion, a third body portion, a distal cone portion and a distal waist portion. The second body portion may comprise a stepped-down section. An inflated diameter of the second body portion may be less than an inflated diameter of the first body portion or the third body portion. An outer surface of the second body portion may be provided with at least one implement, such as a blade or stiffening member.

25 Claims, 4 Drawing Sheets

U.S. PATENT DOCUMENTS

| | | | |
|---|---|---|---|
| 6,402,778 B2 | 6/2002 | Wang | 623/1.11 |
| 6,425,882 B1 | 7/2002 | Vigil | 604/99.01 |
| 6,488,653 B1 * | 12/2002 | Lombardo | 604/103.06 |
| 6,517,514 B1 | 2/2003 | Campbell | 604/96.01 |
| 6,632,231 B2 | 10/2003 | Radisch, Jr. | 606/159 |
| 6,730,105 B2 | 5/2004 | Shiber | 606/159 |
| 6,746,463 B1 | 6/2004 | Schwartz | 606/159 |
| 7,083,639 B2 * | 8/2006 | Guinan et al. | 623/1.1 |
| 2001/0008976 A1 | 7/2001 | Wang | 623/1.11 |
| 2002/0009668 A1 | 1/2002 | Nishimura et al. | 430/270.1 |
| 2002/0010489 A1 * | 1/2002 | Grayzel et al. | 606/194 |
| 2002/0095203 A1 * | 7/2002 | Thompson et al. | 623/1.11 |
| 2002/0120320 A1 * | 8/2002 | Wang et al. | 623/1.11 |
| 2002/0120321 A1 * | 8/2002 | Gunderson et al. | 623/1.11 |
| 2003/0055378 A1 * | 3/2003 | Wang et al. | 604/103.07 |
| 2003/0060832 A1 * | 3/2003 | Guinan et al. | 606/108 |
| 2003/0236563 A1 * | 12/2003 | Fifer | 623/1.11 |
| 2004/0034384 A1 | 2/2004 | Fukaya | 606/191 |
| 2005/0038383 A1 | 2/2005 | Kelley et al. | 604/103.06 |

FOREIGN PATENT DOCUMENTS

| | | |
|---|---|---|
| EP | 1062966 A1 * | 12/2000 |
| WO | 030 68 307 | 8/2003 |

* cited by examiner

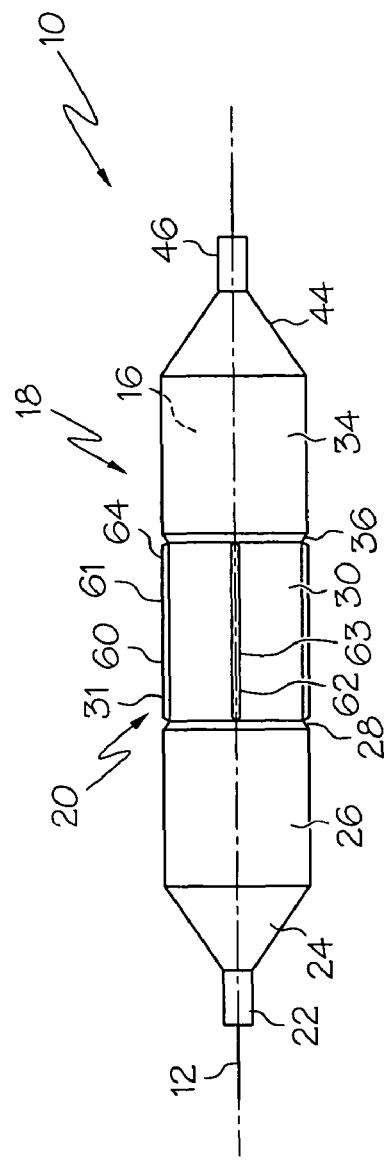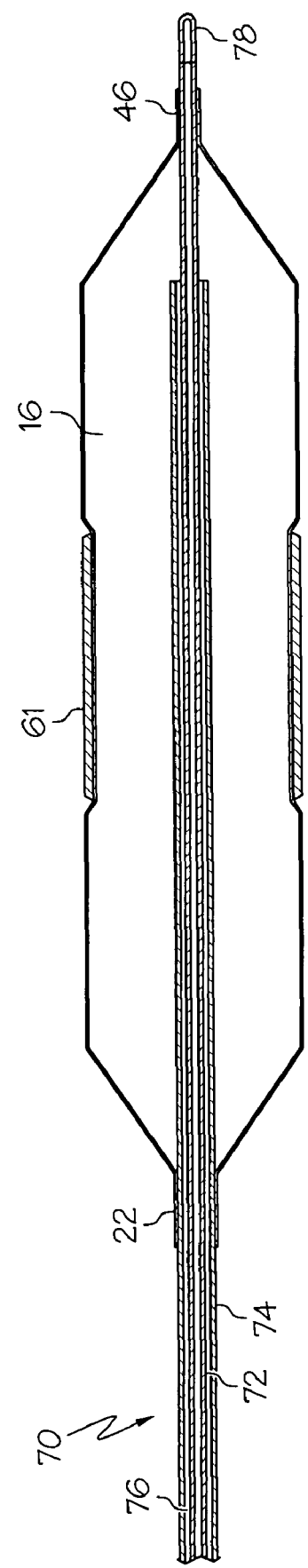

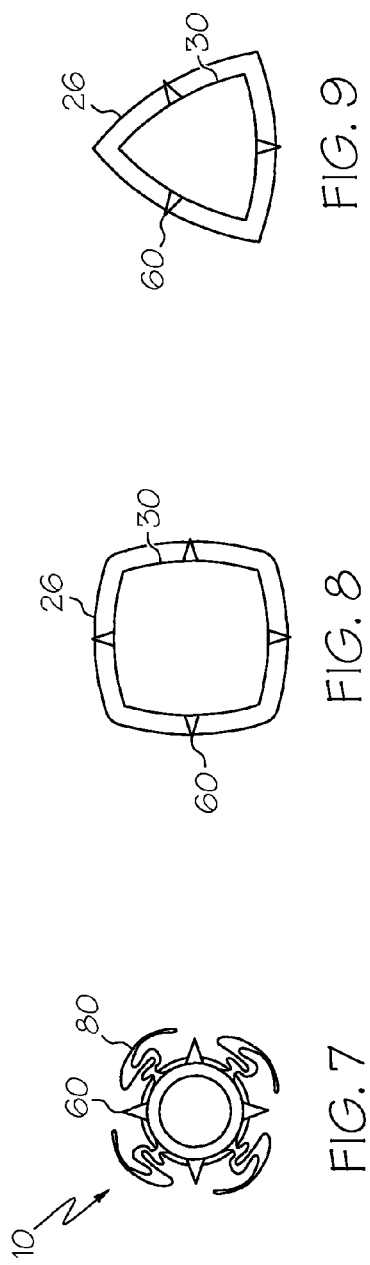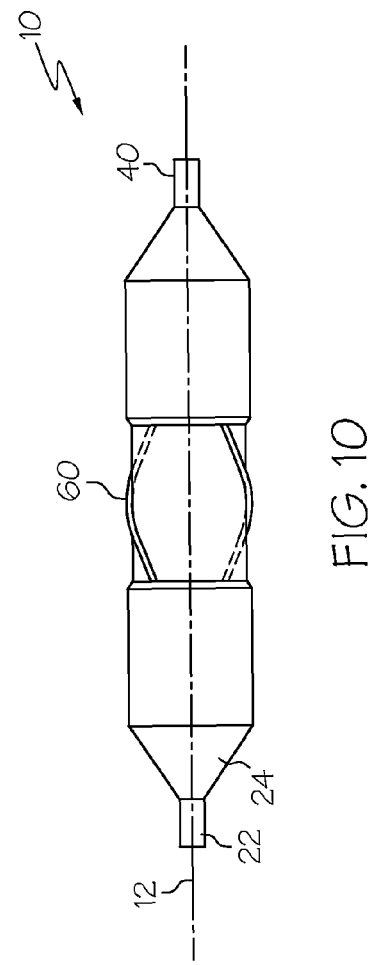

US 7,879,053 B2

BALLOON WITH STEPPED SECTIONS AND IMPLEMENTS

BACKGROUND OF THE INVENTION

This invention relates generally to balloon catheters, which are known in the art, and more specifically to balloon catheters which may be provided with implements to aid in the treatment of blockages, such as stiffening members, cutting blades and the like. In some embodiments, a balloon catheter may be used to deliver an expandable medical device, such as a stent, to a treatment area.

Percutaneous transluminal coronary angioplasty (PTCA) is a procedure which is well established for the treatment of blockages in the coronary and peripheral arteries.

A widely used form of percutaneous angioplasty makes use of a dilatation balloon catheter. The provision of cutting blades upon the balloon facilitates the cutting and dilation of stenoses. An example of a balloon catheter with a cutting edge is disclosed in U.S. Pat. No. 5,616,149, the entire disclosure of which is incorporated herein by reference in its entirety.

The use of stents in bodily lumen is also known. A stent is typically delivered in an unexpanded state to a desired location in a bodily lumen via a medical device such as a catheter. Once the stent is at the desired bodily location, it is either expanded with a balloon or other suitable device or allowed to expand by, for example, withdrawing a restraining sheath.

There remains a need for inventive catheter balloons which provide superior performance over prior art balloons, for example when treating vessel blockages and/or delivering medical devices to a treatment area.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, a catheter balloon may comprise a proximal waist portion, a proximal cone portion, a first body portion having a first inflated cross-sectional area, a second body portion having a second inflated cross-sectional area and at least one stiffening member, a third body portion having a third inflated cross-sectional area, a distal cone portion and a distal waist portion. The second inflated cross-sectional area may be less than the first inflated cross-sectional area.

In some embodiments the second body portion may include an outer surface, and at least one stiffening member may be attached to the outer surface. In some embodiments the second body portion may include an outer surface, and at least one atherotome may be attached to the outer surface. In some embodiments, both atherotomes and stiffening members may be attached to the outer surface.

In some embodiments, a catheter balloon may comprise a proximal waist portion, a proximal cone portion, a first body portion having a first inflated cross-sectional area, a second body portion having a second inflated cross-sectional area and at least one blade, a third body portion having a third inflated cross-sectional area, a distal cone portion and a distal waist portion. The second inflated cross-sectional area is less than the first inflated cross-sectional area.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 1 is a side view of an embodiment of a catheter balloon.

FIG. 2 is a longitudinal cross-sectional view of an embodiment of a balloon catheter.

FIG. 7 shows a cross-sectional view of an embodiment of a deflated catheter balloon having folded portions.

FIG. 8 shows a cross-sectional view of an embodiment of an inflated catheter balloon.

FIG. 9 shows a cross-sectional view of another embodiment of an inflated catheter balloon.

FIG. 10 shows another embodiment of a catheter balloon, wherein the balloon includes a blade that spirals helically.

DETAILED DESCRIPTION OF THE INVENTION

Figure 3:
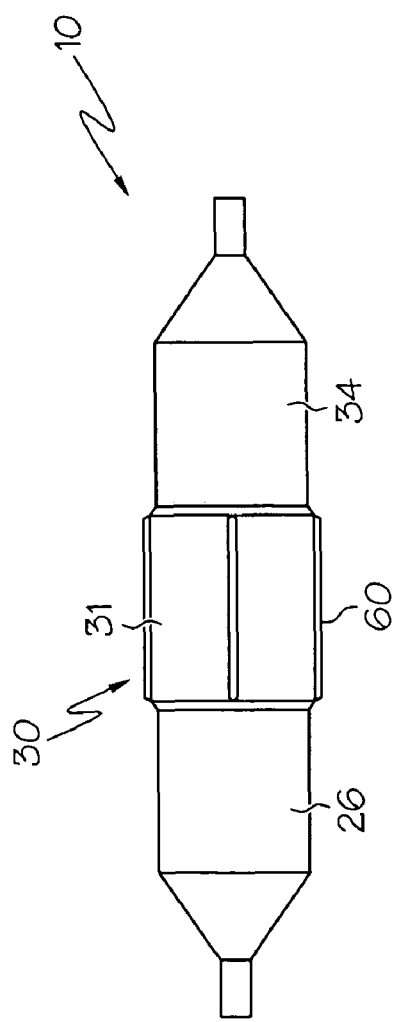
FIG. 3 shows a side view of another embodiment of a catheter balloon.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of an inventive catheter balloon 10. The balloon 10 may comprise a body section 18 having an inner lumen 16. The body section 18 may include a stepped down region 20 having an inflated diameter that is less than the inflated diameter of regions adjacent to the stepped down region 20.

The balloon 10 may include a proximal waist portion 22, a proximal cone portion 24, a first body portion 26, a second body portion 30, a third body portion 34, a distal cone portion 44 and a distal waist portion 46. The balloon 10 may be inflatable from a first, uninflated or unexpanded state to a second, inflated or expanded state. In an inflated state, the second body portion 30 may have an inflated size or diameter which is less than an inflated size or diameter of the first body portion 26 or the third body portion 34. An inflated size or diameter of the first body portion 26 may be substantially equal to the inflated size or diameter of the third body portion 34. The balloon 10 may further include an intermediate proximal cone portion 28 between the first body portion 26 and the second body portion 30, and an intermediate distal cone portion 36 between the second body portion 30 and the third body portion 34.

The second body portion may include an outer surface 31. At least one and desirably a plurality of implements 60 may be provided on the balloon 10 and may be affixed to the outer surface 31. Implements 60 may be affixed to the balloon 10 using any suitable method, such as adhesive bonding or thermal bonding via the application of RF energy, IR energy, UV energy, laser energy, ultra-sonic energy, electrical energy, and any combination thereof. In some embodiments, the outer surface 31 and an implement 60 may be provided with interlocking surface features for mutual securement. In some embodiments, an implement 60 may be imbedded in a substrate material, such as a polyurethane pad, and the substrate may be secured to the balloon 10 as disclosed in U.S. Pat. No. 5,320,634, the entire disclosure of which is incorporated herein by reference in its entirety. In some embodiments, the trailing and/or leading edges or outer corners of implements 60 may be rounded to aid in deliverability of the balloon 10 during insertion, possible repositioning and retraction.

Implements 60 may serve a variety of purposes, such as stiffening the balloon, aiding in the dilation of a lesion, aiding in the expansion of a stent, preventing "watermelon seeding" or translocation of the balloon 10 with respect to a lesion during inflation, etc. In some embodiments an implement 60 may comprise a stiffening member 64 which may provide additional stiffness to the balloon 10. When using the balloon 10 to dilate a lesion, a stiffening member 64 may further provide localized areas of greater stress to the lesion, for example in a situation where the stiffening member 64 is in contact with the lesion before any portion of the outer surface 31 of the second body portion 30 contacts the lesion. The localized areas of greater stress may help to separate portions of the lesion and to dilate the lesion.

In some embodiments, a balloon 10 may be used to expand a stent. Stiffening members 64 may contact a stent and aid in providing for proper and uniform expansion of the stent.

Stiffening members 64 may comprise any suitable material and desirably provide greater stiffness than the balloon 10 material. In some embodiments, a stiffening member 64 may comprise a plastic or polymeric material. In some embodiments, a stiffening member 64 may comprise a metal, such as a metallic wire. In some embodiments, a stiffening member 64 may comprise a shape-memory material, such as nitinol and/or a shape memory polymer.

In some embodiments, an implement 60 may comprise an atherotome or blade 62. Each blade 62 may include a sharp cutting edge 63. A blade 62 may comprise any suitable biocompatible material capable of maintaining a cutting edge, such as stainless steel, AerMet® metal alloy available from Carpenter Specialty Alloys, 101 West Bern Street, Reading, Pa. 19601, other suitable metals and/or alloys and suitable polymers. In at least one embodiment, a blade 62 may be at least partially constructed of a shape memory material, such as nitinol and/or a shape memory polymer.

In embodiments where an implement 60 comprises a blade 62 and the balloon 10 is used to dilate a lesion, the design of the balloon 10 desirably helps to prevent trauma to a vessel wall. In embodiments where a blade 62 is secured to a stepped down region 20 or second body portion 30 and the balloon 10 is inflated to a state as depicted in FIG. 1 within a vessel, the outer surfaces of the first body portion 26 and the third body portion 34 may abut the vessel wall. Desirably, an outer cutting edge 63 of the blade 62 may abut the vessel wall without penetrating into the vessel wall.

Although the second body portion 30 desirably has an inflated diameter that is less than the inflated diameter of adjacent body portions (i.e. 26, 34), the second body portion 30 and implements 60 attached thereto will be used in dilating a lesion. Because the lumen diameter through an undilated lesion is generally substantially smaller than the inflated diameter of the second body portion 30, portions of a lesion may extend into the stepped down region 20 of the balloon 10 during inflation. Portions of the lesion may abut implements 60 and/or the outer surface 31 of the second body portion 30, and may be dilated as the balloon 10 is inflated.

An implement 60 may have any suitable shape and orientation on the balloon 10, such as parallel to the central longitudinal axis 12 of the balloon 10 or oriented at an angle to the longitudinal axis 12 of the balloon 10. In some embodiments, an implement 60 may span the length of the body portion of the balloon 10 to which the implement is attached (for example, referring to FIG. 1, an implement 60 may span the entire length of the second body portion 30). In some embodiments, an implement 60 may be segmented along its length. In some embodiments, implements 60 may spiral helically around a portion of the balloon 10 such as described in U.S. patent application Ser. No. 10/879,894, the entire disclosure of which is incorporated herein by reference.

Multiple implements 60 included on a balloon 10 may have similar shapes and orientations or dissimilar shapes and orientations. Any number of implements 60 may be provided on a balloon 10. Implements 60 may be positioned about the balloon 10 at any desirable spacing, and in some embodiments, may be evenly spaced-bout the circumference of the body portion to which they are attached.

Individual implements 60 included on a balloon 10 may comprise any embodiment of an implement 60. For example, in some embodiments, a balloon 10 may include a plurality of implements 60. A portion of the total number of implements 60 may comprise stiffening members 64, and a portion of the total number of implements 60 may comprise blades 62. In some embodiments, blades 62 and stiffening members 64 may alternate about a body portion of the balloon 10.

Each implement 60 may include an outer edge 61 which may be the outermost portion of the implement 60 as measured in a radial direction of the balloon 10. When an implement 60 comprises a blade 62, the outer edge 61 may comprise a cutting edge 63.

When the balloon 10 is in an inflated state, the outer edge 61 of an implement 60 is desirably located radially outward from the outer surface 31 of the body portion of the balloon 10 to which the implement 60 is attached. In some embodiments, the outer edge 61 of an implement 60 may extend a lesser distance from the longitudinal axis 12 than an outer surface of a body portion (i.e. 26, 34) that is adjacent to the body portion (i.e. 30) to which the implement 60 is attached. Thus, in some embodiments, the outer edge 61 of an implement 60 does not comprise an outermost portion of an inflated balloon 10.

In some embodiments, the outer edge 61 of an implement 60 may extend the same distance from the longitudinal axis 12 as an outer surface of a body portion (i.e. 26, 34) that is adjacent to the body portion (i.e. 30) to which the implement 60 is attached. Thus, in some embodiments, the outer edge 61 of an implement 60 may be aligned with an outer surface of an adjacent body portion (i.e. 26, 34) when the balloon 10 is inflated.

In some embodiments, the outer edge 61 of an implement 60 may extend a greater distance from the longitudinal axis 12 than an outer surface of a body portion (i.e. 26, 34) that is adjacent to the body portion (i.e. 30) to which the implement 60 is attached. Thus, in some embodiments, an implement 60 may comprise an outermost portion of an inflated balloon 10.

The outer edges 61 of multiple implements 60 included on a balloon 10 may all extend an equal distance from the central longitudinal axis 12 of the balloon 10. In some embodiments, the outer edges 61 of various implements may be at differing distances from the central longitudinal axis 12 of the balloon 10.

FIG. 2 shows a sectional view of an embodiment of a balloon 10. The balloon 10 may be attached to a catheter 70. Any suitable catheter may be used with various embodiments of the balloon 10.

A catheter shaft 70 may comprise an inner shaft 72 and an outer shaft 74. An inflation lumen 76 may be defined between the inner shaft 72 and the outer shaft 74. The inflation lumen 76 may be in fluid communication with the inner lumen 16 of the balloon 10. The proximal waist portion 22 of the balloon 10 may be secured to the outer shaft 74, and the distal waist portion 46 of the balloon 10 may be secured to the inner shaft 72. The catheter 70 may further include a distal tip 78.

FIG. 3 shows another embodiment of a balloon 10, wherein the balloon 10 may include a stepped compliance curve. Catheter balloons having stepped compliance curves are discussed, for example, in U.S. Pat. Nos. 6,402,778 and 6,290,485, the entire disclosures of which are incorporated herein by reference in their entireties. A balloon 10 having a stepped compliance curve may have a first inflated state at a first internal fluid pressure and a second inflated state at a second internal fluid pressure. The second internal fluid pressure may be higher than the first internal fluid pressure.

When the balloon 10 is in the first inflated state, the balloon 10 may assume a first inflated shape, for example a shape similar to the shape depicted in FIG. 1 having a stepped down region 20. The outer surface 31 of the second body portion 30 may assume a first inflated diameter. An outer surface of the first body portion 26 may assume a diameter that is larger than that of the outer surface 31 of the second body portion 30, and an outer surface of the third body portion 34 may assume a diameter that is larger than that of the outer surface 31 of the second body portion 30. In some embodiments, the diameter of the first body portion 26 and the diameter of the third body portion 34 may be equal in the first inflated state.

When the balloon 10 is in the second inflated state, the balloon 10 may assume a second inflated shape, for example a shape as depicted in FIG. 3. As the balloon 10 transitions from the first inflated state to the second inflated state, the outer surface 31 of the second body portion 30 may assume a second, larger diameter. The diameter of the second body portion 30 in the second inflated state may be larger than the diameter of the first body portion 26 and/or the diameter of the third body portion 34.

Figure 4:
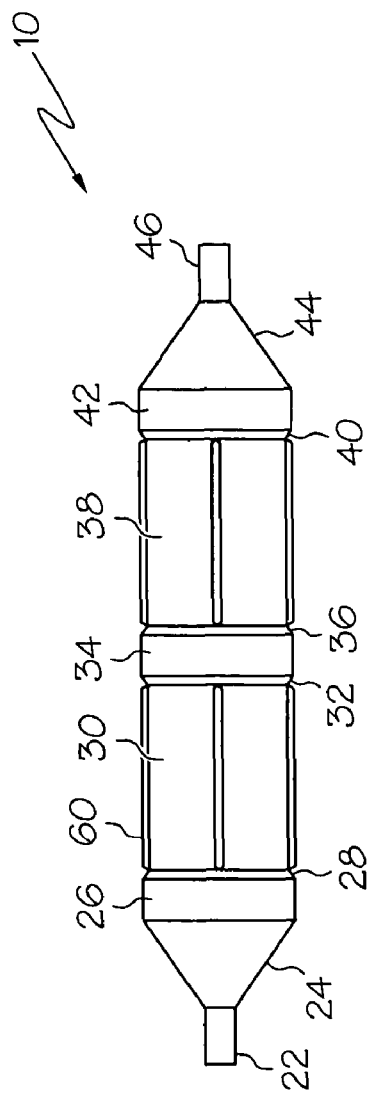
FIG. 4 shows a side view of another embodiment of a catheter balloon.

FIG. 4 shows another embodiment of a balloon 10. The balloon 10 may include a first body portion 26, a second body portion 30, a third body portion 34, a fourth body portion 38 and a fifth body portion 42. In an inflated state, the diameter of the second body portion 30 and the diameter of the fourth body portion 38 may be smaller than the diameter of the first body portion 26, the third body portion 34 and/or the fifth body portion 42. In some embodiments, the inflated diameter of the second body portion 30 may be the same as the inflated diameter of the fourth body portion 38. In some embodiments, the inflated diameter of the first body portion 26, the third body portion 34 and the fifth body portion 42 may be the same.

The balloon 10 may further include a proximal waist 22, a proximal cone 24, a distal cone 44 and a distal waist 46. The balloon 10 may also include a first intermediate proximal cone portion 28 between the first body portion 26 and the second body portion 30, a second intermediate proximal cone portion 32 between the second body portion 30 and the third body portion 34, a first intermediate distal cone portion 36 between the third body portion 34 and the fourth body portion 38, and a second intermediate distal cone portion 40 between the fourth body portion 38 and the fifth body portion 42.

The second body portion 30 and the fourth body portion 38 may be provided with implements 60 as herein described. Implements 60 provided on the second body portion 30 may be similar to or dissimilar from implements 60 provided on the fourth body portion 38. For example, in some embodiments, the second body portion 30 may have a greater number of implements 60 than the fourth body portion 38. In some embodiments, the second body portion 30 may have blades 62 while the fourth body portion 38 may have stiffening members 64, or vice versa. In some embodiments, both the second body portion 30 and the fourth body portion 38 may have alternating blades 62 and stiffening members 64.

Figure 5:
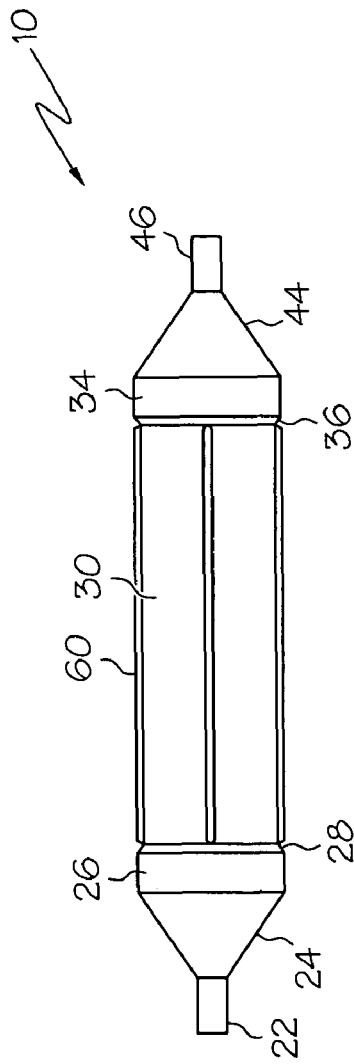
FIG. 5 shows a side view of another embodiment of a catheter balloon.

FIG. 5 shows another embodiment of a balloon 10. The balloon 10 may include a proximal waist portion 22, a proximal cone portion 24, a first body portion 26, a second body portion 30, a third body portion 34, a distal cone portion 44 and a distal waist portion 46. In an inflated state, the second body portion 30 may have an inflated size or diameter which is less than an inflated size or diameter of the first body portion 26 or the third body portion 34. An inflated size or diameter of the first body portion 26 may be substantially equal to the inflated size or diameter of the third body portion 34. The balloon 10 may further include an intermediate proximal cone portion 28 between the first body portion 26 and the second body portion 30, and an intermediate distal cone portion 36 between the second body portion 30 and the third body portion 34.

The second body portion 30 may span substantially the entire length of the balloon 10 between the proximal cone 24 and the distal cone 44. The second body portion 30 may span a greater distance along the longitudinal axis of the balloon 10 than either the first body portion 26 or the third body portion 34.

Implements 60 as herein described may be provided on the second body portion 30. Implements 60 may span substantially the entire length of the second body portion 30, and may thus span substantially the entire length of the balloon 10 between the proximal cone 24 and the distal cone 44.

Figure 6:
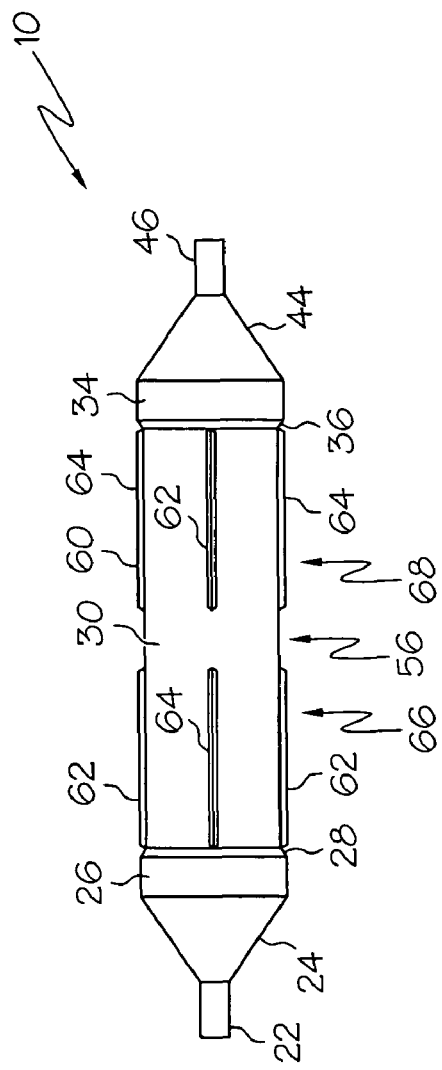
FIG. 6 shows a side view of another embodiment of a catheter balloon.

FIG. 6 shows another embodiment of a balloon 10 which may comprise a proximal waist portion 22, a proximal cone portion 24, a first body portion 26, a second body portion 30, a third body portion 34, a distal cone portion 44 and a distal waist portion 46. An intermediate proximal cone portion 28 may be provided between the first body portion 26 and the second body portion 30, and an intermediate distal cone portion 36 may be provided between the second body portion 30 and the third body portion 34.

Implements 60 as herein described may be provided on the second body portion 30. Multiple implements 60 may be provided along the length of the second body portion. In some embodiments, a first set 66 of implements 60 may be provided spanning a first portion of the length of the second body portion 30, and a second set 68 of implements 60 may be provided spanning a second portion of the length of the second body portion 30.

Implements 60 provided in the first set 66 may be similar to or dissimilar from implements 60 provided in the second set 68. For example, in some embodiments, the first set 66 may have a greater number of implements 60 than the second set 68. In some embodiments, the first set 66 may have blades 62 while the second set 68 may have stiffening members 64, or vice versa. In some embodiments, both the first set 66 and the second set 68 may have alternating blades 62 and stiffening members 64, such as shown in FIG. 6. In some embodiments, a blade 62 of the first set 66 may be longitudinally adjacent to a stiffening member 64 of the second set 68.

Using multiple implements 60 along the length of the second body portion 30 provides a flexible portion 56 along the second body portion 30, wherein no implements 60 are present to stiffen the flexible portion 56. This provides greater longitudinal flexibility to the balloon 10 and helps to allow the balloon 10 to traverse a tortuous bodily lumen.

FIG. 7 shows an embodiment of a balloon 10 in an unexpanded state. Portions of the balloon 10 spanning between circumferentially adjacent implements 60 may be folded into folded portions 80 and positioned between the adjacent implements 60. Further examples of folding configurations for unexpanded catheter balloons are disclosed in U.S. Pat. No. 5,226,887, U.S. Pat. No. 5,320,634 and U.S. Pat. No. 6,425,882, the entire disclosures of which are incorporated herein by reference in their entireties.

Any embodiment of a balloon 10 as described herein may be provided with any desirable cross-sectional shape. All teachings with regard to the diameter of various sections of a balloon 10 having a circular cross-sectional shape may be analogized to the size or cross-sectional area of various sections of a balloon 10 having non-circular cross-sectional shapes.

FIG. 8 shows a cross-sectional view of an embodiment of a balloon 10 having a substantially square cross-sectional shape. A first body portion 26 may have a greater size or cross-sectional area in the expanded state than a second body portion 30.

FIG. 9 shows a cross-sectional view of an embodiment of a balloon 10 having a substantially triangular cross-sectional shape. A first body portion 26 may have a greater size or cross-sectional area in the expanded state than a second body portion 30.

A balloon 10 may be made of any suitable balloon material including compliant and non-compliant materials and combinations thereof. Some examples of suitable materials for constructing the balloon body 18 include but are not limited to: low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers; copolymer polyolefin material available from E.I. DuPont de Nemours and Co. (Wilmington, Del.), under the trade name SurlynJ; ionomer and a polyether block amide available under the trade name PEBAXJ; high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane; one or more liquid crystal polymers; and combinations of one or more of any of the above, as well as others.

In some embodiments the catheter balloon 10 may be configured to deliver one or more therapeutic agents to a stenosis, aneurysm or lesion within a body lumen. In some embodiments at least a portion of a blade 62 may be configured to include one or more holes, notches, or other surface features to which one or more therapeutic agents may be placed for delivery to the aneurysm site. A therapeutic agent may be placed on the blade(s) 62 and/or the exterior surface of a balloon 10 in the form of one or more coatings. In at least one embodiment the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The invention is further drawn to methods of making a balloon 10 as described herein. For example, a method may comprise forming or otherwise providing a balloon having a stepped down region 20 or a first body portion 26, a second body portion 30 and a third body portion 34. At least one implement 60, such as a stiffening member 64 or blade 62, may be affixed to the outer surface of the stepped down region 20 or second body portion 30.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter balloon comprising:
   a proximal waist portion;

a proximal cone portion attached to the proximal waist portion;
a distal waist portion;
a distal cone portion attached to the distal waist portion; and
a body section extending between the proximal cone portion and the distal cone portion, wherein in a fully inflated state the body section comprises:
a first body portion having a first inflated cross-sectional area;
a second body portion located distal to the first body portion, the second body portion having a second inflated cross-sectional area and at least one stiffening member fixedly bonded to an outer surface of the second body portion, each stiffening member occupying only a portion of a circumference of the second body portion; and
a third body portion located distal to the second body portion, the third body portion having a third inflated cross-sectional area;
wherein the second inflated cross-sectional area is less than the first inflated cross-sectional area;
wherein the balloon defines a longitudinal axis and a radial distance between the longitudinal axis and an outer surface of said at least one stiffening member is at least equal to a radial distance between the longitudinal axis and an outer surface of the first body portion when the balloon is inflated;
wherein each stiffening member comprises an elongate structure extending parallel to the longitudinal axis of the balloon.

2. The catheter balloon of claim 1, wherein the radial distance between the longitudinal axis and an outer surface of said at least one stiffening member is greater than the radial distance between the longitudinal axis and an outer surface of the first body portion when the balloon is inflated.

3. The catheter balloon of claim 1, further comprising:
an intermediate proximal cone portion located between the first body portion and the second body portion; and
an intermediate distal cone portion located between the second body portion and the third body portion.

4. The catheter balloon of claim 1, wherein the second body portion further includes at least one atherotome attached to its outer surface.

5. The catheter balloon of claim 4, wherein stiffening members and atherotomes alternate about the periphery of said second body portion.

6. The catheter balloon of claim 1, wherein the third inflated cross-sectional area is substantially equal to the first inflated cross-sectional area.

7. The catheter balloon of claim 1, the body section further comprising a fourth body portion located distal to the third body portion, the fourth body portion having a fourth inflated cross-sectional area and at least one stiffening member; and
a fifth body portion located distal to the fourth body portion, the fifth body portion having a fifth inflated cross-sectional area.

8. The catheter balloon of claim 7, further comprising:
a first intermediate proximal cone portion located between the first body portion and the second body portion;
a second intermediate proximal cone portion located between the second body portion and the third body portion;
a first intermediate distal cone portion located between the third body portion and the fourth body portion; and
a second intermediate distal cone portion located between the fourth body portion and the fifth body portion.

9. The catheter balloon of claim 7, wherein the second body portion includes an outer surface, the fourth body portion includes an outer surface, at least one stiffening member is fixedly attached to the outer surface of the second body portion, and at least one stiffening member is fixedly attached to the outer surface of the fourth body portion.

10. The catheter balloon of claim 9, wherein the second body portion further includes at least one atherotome, and the fourth body portion further includes at least one atherotome.

11. The catheter balloon of claim 10, wherein stiffening members and atherotomes alternate about the periphery of said second body portion and said fourth body portion.

12. The catheter balloon of claim 7, wherein the third inflated cross-sectional area and the fifth inflated cross-sectional area are substantially equal to the first inflated cross-sectional area.

13. The catheter balloon of claim 7, wherein the second inflated cross-sectional area is substantially equal to the fourth inflated cross-sectional area.

14. The catheter balloon of claim 1, wherein the second body portion has a substantially square cross-sectional shape.

15. The catheter balloon of claim 1, wherein the second body portion has a substantially triangular cross-sectional shape.

16. The catheter balloon of claim 1, wherein the outer edge of said stiffening member extends radially outward beyond an outer surface of the third body portion.

17. The catheter balloon of claim 1, wherein a plurality of stiffening members are fixedly attached to an outer surface of the second body portion, the stiffening members spaced apart from one another about the circumference of the second body portion.

18. The catheter balloon of claim 1, wherein the radial distance between the longitudinal axis and the outer surface of said at least one stiffening member is approximately equal to the radial distance between the longitudinal axis and the outer surface of the first body portion when the balloon is inflated.

19. A catheter balloon comprising:
a proximal waist portion;
a proximal cone portion attached to the proximal waist portion;
a distal waist portion;
a distal cone portion attached to the distal waist portion; and
a body section extending between the proximal cone portion and the distal cone portion, wherein in a fully inflated state the body section comprises:
a first body portion having a first inflated cross-sectional area;
a second body portion located distal to the first body portion, the second body portion having a second inflated cross-sectional area and at least one stiffening member fixedly bonded to an outer surface of the second body portion, the second inflated cross-sectional area being constant along the length of the second body portion; and
a third body portion located distal to the second body portion, the third body portion having a third inflated cross-sectional area;
wherein the second inflated cross-sectional area is less than the first inflated cross-sectional area;
wherein the balloon defines a longitudinal axis and a radial distance between the longitudinal axis and an outer surface of said at least one stiffening member is at least equal to a radial distance between the longitudinal axis and an outer surface of the first body portion when the balloon is inflated; and wherein the second body portion spans substantially the entire length of the balloon between the proximal cone portion and the distal cone portion.

20. A catheter balloon comprising:

a proximal waist portion;

a proximal cone portion attached to the proximal waist portion;

a distal waist portion;

a distal cone portion attached to the distal waist portion; and a body section extending between the proximal cone portion and the distal cone portion, wherein in a fully inflated state the body section comprises:
- a first body portion having a first inflated cross-sectional area;
  - a second body portion having a second inflated cross-sectional area and at least one blade fixedly bonded to its outer surface; and
- a third body portion having a third inflated cross-sectional area;
  - wherein the second inflated cross-sectional area is less than the first inflated cross-sectional area;

wherein the balloon defines a longitudinal axis and a radial distance between the longitudinal axis and an outer edge of said at least one blade is at least equal to a radial distance between the longitudinal axis and an outer surface of the first body portion when the balloon is inflated;

wherein the body section has a length extending between the proximal cone portion and the distal cone portion, wherein the second body portion extends a majority of the length of the body section.

21. The catheter balloon of claim 20, wherein said at least one blade spirals helically in a direction around the second body portion.

22. The catheter balloon of claim 21, wherein the outer edge of the blade extends outward in a radial direction beyond the outer surface of the first body portion.

23. The catheter balloon of claim 21, wherein the second body portion spans substantially the entire length of the balloon between the proximal cone portion and the distal cone portion.

24. The catheter balloon of claim 20, further comprising:
an intermediate proximal cone portion located between the first body portion and the second body portion; and
an intermediate distal cone portion located between the second body portion and the third body portion.

25. The catheter balloon of claim 20, wherein the radial distance between the longitudinal axis and the outer surface of said at least one blade is approximately equal to the radial distance between the longitudinal axis and the outer surface of the first body portion when the balloon is inflated.

* * * * *